United States Patent [19]

Hoederath et al.

[11] Patent Number: 4,842,856
[45] Date of Patent: Jun. 27, 1989

[54] PARENTERAL SOLUTION

[75] Inventors: Wolfgang Hoederath, Lindlar-Linde; Hans J. Ahr; Klaus Bühner, both of Wuppertal; Ahmed Hegasy, Leverkusen; Manfred Winter, Cologne, all of Fed. Rep. of Germany

[73] Assignee: Bayer Aktiengesellschaft, Leverkusen, Fed. Rep. of Germany

[21] Appl. No.: 142,619

[22] Filed: Jan. 11, 1988

[30] Foreign Application Priority Data

Jan. 24, 1987 [DE] Fed. Rep. of Germany ....... 3702105

[51] Int. Cl.$^4$ .................... A61K 9/00; A61K 47/00; A61K 31/44; A61K 9/22
[52] U.S. Cl. .................................... 424/101; 514/250; 514/258; 514/773; 514/776; 514/938; 530/353; 530/363; 530/386; 530/387; 530/392; 530/394; 530/830
[58] Field of Search ............... 514/258, 773, 250, 776, 514/937, 938; 530/353, 363, 386, 387, 392, 394, 830, 937, 938; 424/101

[56] References Cited

U.S. PATENT DOCUMENTS

| | | | |
|---|---|---|---|
| 4,499,073 | 2/1985 | Tenold | 424/101 |
| 4,548,938 | 10/1985 | Kennis et al. | 514/258 |
| 4,597,966 | 6/1986 | Zolton et al. | 424/101 |

FOREIGN PATENT DOCUMENTS

| | | |
|---|---|---|
| 0123850 | 11/1984 | European Pat. Off. . |
| 0126315 | 11/1984 | European Pat. Off. . |
| 0140255 | 5/1985 | European Pat. Off. . |
| 427669 | 4/1926 | Fed. Rep. of Germany . |

Primary Examiner—John Kight
Assistant Examiner—C. Azpuru
Attorney, Agent, or Firm—Sprung Horn Kramer & Woods

[57] ABSTRACT

Parenteral solutions comprising
(a) a sparingly soluble medicament active compound,
(b) a solvent consisting of
   (i) 5-100 M/V % of an organic solvent or of a mixture of organic solvents and
   (ii) 0-95 W/V % of water,
(c) A 0.5-30 W/V % strength aqueous solution of a human serum protein and customary auxiliaries and/or excipients, 1 to 40,000 parts by weight, preferably 25 to 30,000 parts by weight of solvent (b) and 1 to 1,000,000 parts by weight, preferably 50 to 40,000 parts by weight, of human serum protein solution (c) being present per part by weight of medicament active compound.

The sparingly soluble medicament active compounds which can be used have a solubility in water of between 1 $\mu$g and 10 g, preferably between 10 $\mu$g and 1 g per liter of water. Examples of such medicaments are dihydropyridine compounds and pyrazolones, and muzolimine.

6 Claims, No Drawings

PARENTERAL SOLUTION

Parenteral administration of medicaments, essentially intravenous administration, is only possible in the dissolved form. Formulation of injection and infusion solutions of medicaments of low water-solubility therefore regularly presents difficulties.

In the case of inadequate solubility in water, organic solvents, such as propylene glycol, polyethylene glycol, ethanol, glycerol, polyethylene glycol ricinoleate (Cremophor ® EL) or polyoxyethylene sorbitan fatty acid esters (Tween ®) have previously been added to increase solubility for formulation of parenteral solutions of sparingly soluble medicaments. The effectiveness of this measure is limited, however, by the fact that such organic solvents can be used only low concentrations, since higher concentrations lead to undesirable side effects, such as injection pain, thrombophlebitis and phlebosclerozation Moreover, some solvents lead to side effects, such as anaphylactic shock and hemolysis.

Another possibility of solubilization of medicaments of low water-solubility comprises dissolving the medicament in the oily phase of an emulsion (U.S. Pat. No. 4,073,943). However, a condition of this process is a very good solubility of the medicament in physiologically acceptable oils, such as soya bean oil, which is only guaranteed in the rarest of cases.

The solubilization described in U.S. Pat. No. 4,158,707 with a combination of bile acid and lipoid has the disadvantage of a limited storage life of the solubilizing agent, especially at higher temperatures, and of side effects, such as vomiting, hemolysis and cholestasis, on administration in relatively high doses.

The present invention thus relates to parenteral solutions of sparingly soluble medicaments which contain human serum proteins, the human serum proteins serving as crystallization inhibitors.

Parenteral solutions here are essentially intravenous administrations with medicaments, in particular injection and infusion solutions. Concentrates containing the active compound in suitable organic solvents, such as 1,2-propylene glycol, glycerol, ethanol, polyethylene glycols with average molecular weights of between 200 and 600 and tetrahydrofurfuryl alcohol polyethylene glycol ethers mixed with water, which are diluted with aqueous human serum protein solutions before administration, are in general used for the parenteral solutions according to the invention. Human albumin solutions (USP XXI) or plasma protein fraction solutions (USP XXI) are preferably employed as the human serum protein solutions, and as a rule the latter type delay precipitation of the active compound for longer and also at a higher concentration of the medicament. The serum proteins can also contain $\alpha$-, $\beta$- and $\gamma$-globulins in addition to albumin.

The invention thus relates to a parenteral solution containing
(a) a sparingly soluble medicament active compound,
(b) a solvent consisting of
  (i) 5–100 W/V % of an organic solvent or of a mixture of organic solvents and
  (II) 0–95 W/V % of water,
(c) a 0.5–30 W/V % strength aqueous solution of a human serum protein and customary auxiliaries and/or excipients, 1 to 40,000 parts by weight, preferably 25 to 30,000 parts by weight of solvent (b) and 1 to 1,000,000 parts by weight, preferably 50 to 40,000 parts by weight, of human serum protein solution (c) being present per part by weight of medicament active compound.

The sparingly soluble medicament active compounds which can be used according to the invention in general have a solubility in water of between 1 $\mu$g and 10 g, preferably between 10 $\mu$g and 1 g per liter of water. Examples which may be mentioned are dihydropyridine compounds and pyrazolones, and muzolimine.

The dihydropyridine compounds are of particular importance, especially those with the following general formula

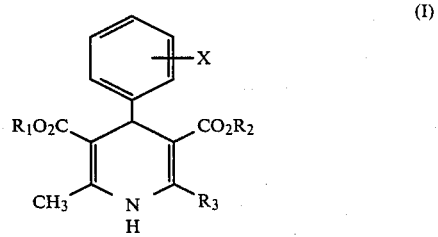

(I)

in which
  $R_1$ denotes $C_1$–$C_4$-alkyl which is optionally substituted by $C_1$–$C_3$-alkoxy,
  $R_2$ denotes $C_1$–$C_{10}$-alkyl which is optionally substituted by $C_1$–$C_3$-alkoxy, trifluoromethyl or N-methyl-N-benzylamino,
  $R_3$ denotes $C_1$–$C_4$-alkyl, cyano or hydroxymethyl and
  X denotes 2- or 3-nitro, 2,3-dichloro or a 2,3-ring member consisting of =N—O—N=.

The compounds of the following table are especially suitable:

(I)

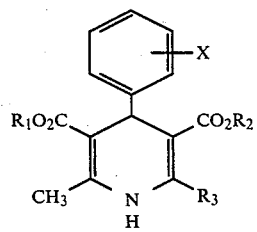

| No. | X | $R^1$ | $R^2$ | $R^3$ | Generic |
|---|---|---|---|---|---|
| 1 | 2-$NO_2$ | $CH_3$ | $CH_3$ | $CH_3$ | Nifedipine |
| 2 | 3-$NO_2$ | $nPrOCH_2CH_2$ | $nPrOCH_2CH_2$ | $CH_3$ | Niludipine |
| 3 | 3-$NO_2$ | $C_2H_5$ | $CH_3$ | $CH_3$ | Nitrendipine |
| 4 | 2-$NO_2$ | $CH_3$ | $(CH_3)_2CHCH_2$ | $CH_3$ | Nisoldipine |

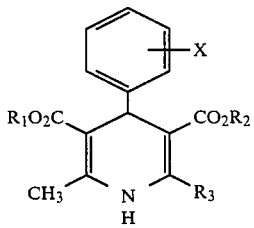

(I)

| No. | X | $R^1$ | $R^2$ | $R^3$ | Generic |
|-----|---|-------|-------|-------|---------|
| 5 | 3-$NO_2$ | $CH(CH_3)_2$ | $(CH_2)_2$—O—$CH_3$ | $CH_3$ | Nimodipine |
| 6 | 3-$NO_2$ | $C_2H_5$ | $C_{10}H_{21}(n)$ | $CH_3$ | |
| 7 | 2-Cl | $CH_3$ | $CH_2$—$CF_3$ | $CH_3$ | |
| 8 | 2-Cl | $C_2H_5$ | $CH_2$—$CF_3$ | $CH_3$ | |
| 9 | 3-$NO_2$ | $CH(CH_3)_2$ | n-PrO—$CH_2$—$CH_2$ | $CH_3$ | |
| 10 | 3-$NO_2$ | $CH_3$ | $C_6H_5CH_2N(CH_3)CH_2CH_2$ | $CH_3$ | Nicradipine |
| 11 | 2,3-$Cl_2$ | $C_2H_5$ | $CH_3$ | $CH_3$ | Felodipine |
| 12 | 2,3=N—O—N= | $C_2H_5$ | $C_2H_5$ | $CH_3$ | |
| 13 | 2,3=N—O—N= | $CH_3$ | $CH(CH_3)_2$ | $CH_3$ | |
| 14 | 3-$NO_2$ | $C_2H_5$ | $C_2H_5$ | $CH_2OH$ | |
| 15 | 3-$NO_2$ | $CH_3$ | $CH_3$ | CN | |
| 16 | 3-$NO_2$ | $CH_3$ | $(CH_2)_3$—$(CF_2)_5$—$CF_3$ | $CH_3$ | | n-Pr = n-Propyl

Ethyl or methyl 2-methyl-4-(4-oxo-2-phenyl-4H-thiochromen-8-yl)-5-oxo-1,4,5,7-tetrahydrofuro-[3,4-b]pyridine-3-carboxylate may furthermore also be mentioned as the dihydropyridine compound.

The human albumin or plasma protein fraction solutions which can be used according to the invention are commercially available in the form of 5, 20 or 25% strength solutions and are described in many pharmacopeias, for example in USP XXI and BP 80, and in Remington's Pharmaceutical Sciences, Mack Publishing Company, Easton Pa.

The parenteral solutions can contain, inter alia, auxiliaries and/or excipients, such as N-acetyl-dl-tryptophan, caprylate, acetate, citrate, glucose and electrolytes, such as the chlorides, phosphates and bicarbonates of sodium, potassium, calcium and magnesium.

They can furthermore contain: acids, bases or buffer substances for adjusting the pH, salts, sugars or polyhydric alcohols for isotonicity and adjustment, preservatives, such as benzyl alcohol or chlorobutanol, and antioxidants, such as sulphites, acetylcysteine or ascorbic acid.

The parenteral solution according to the invention can be prepared by a process in which the medicament active compound is first dissolved in an organic solvent and if appropriate water is also added. This concentrate is then filtered, bottled and diluted with human serum protein solution immediately before administration.

Although the solutions thus obtained are frequently clearly supersaturated, precipitation of the active compound is delayed and usually occurs only after a few hours.

EXPERIMENTAL EXAMPLES

Injection solutions corresponding to this invention can be prepared as follows:

1. concentrate of the insoluble medicament ethyl 2-methyl-4-(4-oxo-2-phenyl-4-H-thiochromen-8-yl)-5-oxo-1,4,5,7-tetrahydrofuro-[3,4-b]-pyridine-3-carboxylate is dissolved in an amount of 0.5 g in a mixture of 600 g of polyethylene glycol 400 and 200 g of ethanol, while stirring and warming. After cooling to 20° C., the loss of ethanol by evaporation is compensated and the mixture is made up to 1 liter with water for injection purposes.

Finished injection solution 8 ml of human albumin 5% or plasma protein fraction 5% are added to 2 ml of the concentrate described above and the components are mixed.

The supersaturated solution ready for administration which is thus obtained is clear and virtually free from particles over a period of several hours since crystallization is delayed by using the protein solution as the dilution medium. If the active compound concentrate is diluted with the corresponding amount of water, immediate precipitation of the medicament occurs.

2. Concentrate of the insoluble medicament 1 g of nifedipine is dissolved by warming in a mixture of 250 g of ethanol and 250 g of polyethylene glycol 400. After cooling and compensating the amount of alcohol which has evaporated, the mixture is made up to 600 ml with water for injection purposes.

Finished injection solution 2.4 ml of 5% strength human albumin or 2.4 ml of 5% strength plasma protein fraction are added to 0.6 ml of this concentrate and the components are mixed.

A nifedipine injection solution which is clear for several hours results.

3. Concentrate of the insoluble medicament 10 g of nisoldipine are dissolved in a mixture of 3,000 g of ethanol and 3,000 g of polyethylene glycol 400, while stirring and warming. After cooling to room temperature, the loss of ethanol by evaporation is compensated and the mixture is made up to 7 liters with water for injection purposes.

Finished injection solution 2.7 ml of human albumin 5% or plasma protein fraction 5% are added to 0.35 ml of the concentrate described above and the components are mixed.

A nisoldipine injection solution which is clear for several hours results.

4. Concentrate of the insoluble medicament 10 g of nitrendipine are dissolved in a mixture of 4,000 g of ethanol and 4,000 g of polyethylene glycol 400, while stirring and warming. After cooling to room temperature, the loss of ethanol by evaporation is compensated and the mixture is made up to 10 liters with water for injection purposes.

Finished injection solution 4.0 ml of human albumin 5% or plasma protein fraction 5% are added to 1.0 ml of the concentrate described above and the components are mixed.

A nitrendipine injection solution which is stable for several hours results.

5. Concentrate of the insoluble medicament 60 g of muzolimine are dissolved in a mixture of 2,000 g of ethanol and 2,000 g of polyethylene glycol 400, while stirring. The mixture is then made up to 5 liters with water for injection purposes Finished injection solution 2.5 ml of human albumin 5% or plasma protein fraction 5% are added to 2.5 ml of the concentrate described above and the components are mixed.

A muzolimine injection solution which is clear for several hours results.

What is claimed is:

1. A parenteral solution comprising
   (a) a sparingly soluble medicament active compound,
   (b) a solvent consisting of
      (i) 5-100 W/V % of an organic solvent or a mixture of organic solvents and
      (ii) 0-95 W/V % of water,
   (c) a 0.5-30 W/V % strength aqueous solution of a human serum protein and customary auxiliaries and/or excipients, 1 to 40,000 parts by weight of solvent (b) and 1 to 1,000,000 parts by weight of human serum protein solution (c) being present per part by weight of said medicament active compound.

2. A parenteral solution according to claim 1, comprising 25 to 30,000 parts by weight of solvent (b) and 50 to 40,000 parts by weight of human serum protein solution (c) per part by weight of medicament active compound.

3. A parenteral solution according to claim 1 comprising a medicament active compound having solubility of between 1 μg and 1 g per liter of water.

4. A parenteral solution according to claim 1, wherein said medicament active compound is a dihydropyridine compound or a pyrazolone compound or muzolimine.

5. A process for the preparation of a parenteral solution comprising
   (a) a sparingly soluble medicament active compound,
   (b) a solvent consisting of
      (i) 5-100 W/V % of an organic solvent or a mixture of organic solvents and
      (ii) 0-95 W/V % of water,
   (c) a 0.5-30 W/V % strength aqueous solution of a human serum protein and customary auxiliaries and/or excipients, 1 to 40,000 parts by weight of solvent (b) and 1 to 1,000,000 parts by weight of human serum protein solution (c) being present per part by weight of medicament active compound, comprising dissolving said medicament active compound in said solvent and then adding said solution of a human serum protein.

6. A parenteral solution according to claim 1, wherein the human serum protein is human albumin or α-, β- and γ-globulins.

* * * * *